(12) United States Patent
Huang et al.

(10) Patent No.: US 10,083,359 B2
(45) Date of Patent: Sep. 25, 2018

(54) METHOD AND DEVICE FOR INCIDENT SITUATION PREDICTION

(71) Applicant: MOTOROLA SOLUTIONS, INC., Chicago, IL (US)

(72) Inventors: Yong Huang, SiChuan (CN); Quan-Wen Du, SiChuan (CN); Jun-Lin Li, SiChuan (CN); Nan-E Li, SiChuan (CN); Guochao Yin, SiChuan (CN); Meng-Tao Zhu, SiChuan (CN)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/525,012

(22) PCT Filed: Apr. 28, 2016

(86) PCT No.: PCT/CN2016/080581
§ 371 (c)(1),
(2) Date: May 5, 2017

(87) PCT Pub. No.: WO2017/185314
PCT Pub. Date: Nov. 2, 2017

(65) Prior Publication Data
US 2018/0204066 A1    Jul. 19, 2018

(51) Int. Cl.
*G06F 19/00*      (2018.01)
*G06K 9/00*       (2006.01)
(Continued)

(52) U.S. Cl.
CPC ..... *G06K 9/00718* (2013.01); *G06K 9/00771* (2013.01); *G06N 5/02* (2013.01);
(Continued)

(58) Field of Classification Search
CPC .. G06K 9/00718; G06K 9/00771; G06N 5/02; G08B 21/02; H04N 7/18
See application file for complete search history.

(56) References Cited

U.S. PATENT DOCUMENTS 4,931,868 A    5/1990   Kadar
7,847,820 B2 * 12/2010  Vallone .............. G06K 9/00288
                                                 348/143

(Continued)

FOREIGN PATENT DOCUMENTS

CN    101016052    8/2007
CN    101329804    12/2008

OTHER PUBLICATIONS

PCT/CN2016/080581 International Search Report and Written Opinion of the International Searching Authority dated Jan. 24, 2017 (8 pages).

(Continued)

*Primary Examiner* — David F Dunphy
(74) *Attorney, Agent, or Firm* — Michael Best & Friedrich LLP

(57) ABSTRACT

A method and device for incident situation prediction. Using the method, a list of objects of interest is generated and stored in a call controller, where each object of interest in the list of objects of interest is associated with at least one of a plurality of incident types. The call controller receives an image stream of an incident and classifies the image stream as one of the plurality of incident types. The call controller selects a subset of objects of interest from the list of objects of interest, the subset of objects of interest associated with the one of the plurality of incident types. The call controller determines whether the image stream includes an object from the subset of objects of interest and generates a notification associated with the object. The notification is (Continued)

transmitted to a set of incident scene devices associated with the incident.

16 Claims, 6 Drawing Sheets

(51) Int. Cl.
    *G06N 5/02*     (2006.01)
    *H04N 7/18*     (2006.01)
    *G08B 21/02*     (2006.01)
    *H04W 4/90*     (2018.01)

(52) U.S. Cl.
    CPC ............... *G08B 21/02* (2013.01); *H04N 7/18* (2013.01); *G06K 2009/00738* (2013.01); *H04W 4/90* (2018.02)

(56) References Cited

U.S. PATENT DOCUMENTS

| | | | |
|---|---|---|---|
| 2007/0288419 A1* | 12/2007 | Strassner | G06N 5/02 706/55 |
| 2008/0294588 A1* | 11/2008 | Morris | G06K 9/00295 706/47 |
| 2012/0170902 A1* | 7/2012 | Zhu | H04N 5/76 386/223 |
| 2013/0208115 A1* | 8/2013 | Park | H04N 7/18 348/143 |
| 2014/0176708 A1* | 6/2014 | Ramakrishnan | G06K 9/624 348/143 |
| 2014/0333775 A1* | 11/2014 | Naikal | H04N 7/181 348/159 |
| 2015/0042467 A1 | 2/2015 | Amis | |
| 2016/0105773 A1 | 4/2016 | Wawrowski et al. | |
| 2016/0342846 A1* | 11/2016 | Gordon | G06K 9/00771 |
| 2017/0193810 A1* | 7/2017 | Cao | G08B 29/185 |
| 2018/0032829 A1* | 2/2018 | Kim | G06K 9/209 |

OTHER PUBLICATIONS

Mansencal et al., "Search of objects of interest in videos," paper (2012) 9 pages, France.

Sivic et al., "Efficient Visual Search for Objects in Videos," manuscript (2008) Proceedings of the IEEE, vol. 96, No. 4 pp. 548-566.

* cited by examiner

| INCIDENT | OBJECT FOR DETECTION | PICTURE | NOTIFICATION |
|---|---|---|---|
| FIRE | GAS TANK | ... | GENERATE ALARM |
| | TRINITROTOLUENE | ... | GENERATE EMERGENCY |
| | OIL TANK | ... | GENERATE ALARM |
| | FIREWORK ROOM | ... | GENERATE ALARM |
| | WATER PUMP | ... | PROMPT INDICATION |
| | FIRE EXTINGUISHER | ... | PROMPT INDICATION |
| GAS LEAK | FIREWORK ROOM | ... | GENERATE ALARM |
| | GAS TANK | ... | GENERATE ALARM |
| HOMICIDE | SWORD | ... | GENERATE ALARM |
| | PISTOL | ... | GENERATE EMERGENCY |

FIG. 6

METHOD AND DEVICE FOR INCIDENT SITUATION PREDICTION

BACKGROUND OF THE INVENTION

During emergency situations, such as, natural disasters, pursuing criminals, processing crime scenes, fighting fires, first responders may be dealing with escalating situations. Providing accurate information to the first responder during these emergency situations will allow the first responders to better manage emergency situations to avoid any escalation. In addition, physical conditions such as, for example, smoke, rain, snow, noise, flashing lights, low light levels, obstructions, and a present point of view may make it difficult to see or otherwise perceive the presence of hazards at incident scenes.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

FIG. 6 illustrates a list of objects of interest in accordance with some embodiments.

Figure 1:
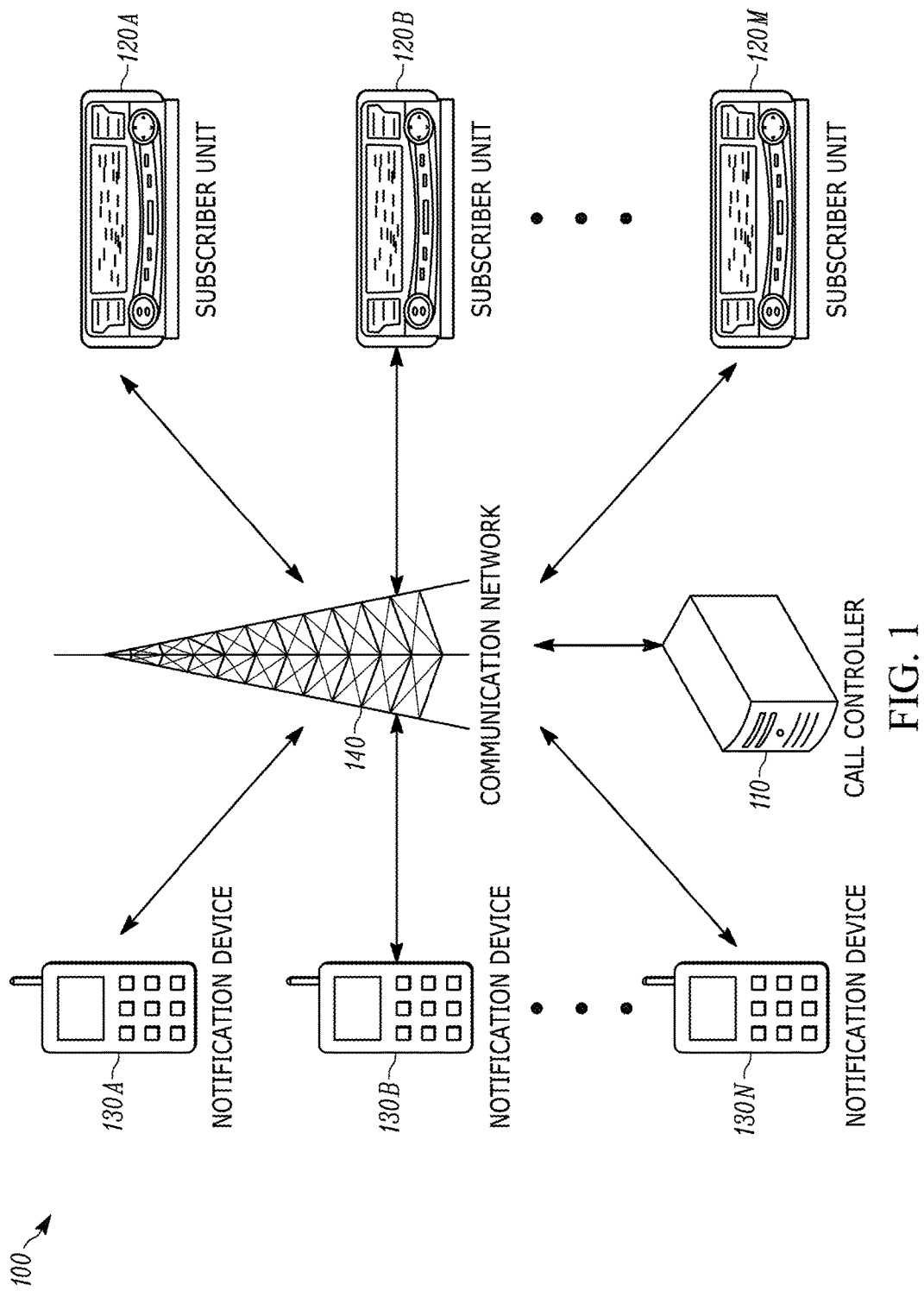
FIG. 1 is a block diagram of a system for incident situation prediction in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

First responders are often equipped with body-worn cameras or similar devices that are capable of capturing images of an incident scene. These cameras and devices may be used for predicting hazardous situations at incident scenes and warning the first responders of these hazardous situations.

One embodiment provides a method of incident situation prediction including generating and storing a list of objects of interest in a memory, where each object of interest in the list of objects of interest is mapped to at least one of a plurality of incident types. The method also includes receiving, with a receiver, an image stream of an incident and classifying, with an electronic processor electrically coupled to the receiver, the image stream as one of the plurality of incident types. The method further includes selecting, from the memory and with the electronic processor, a subset of objects of interest from the list of objects of interest, the subset of objects of interest mapped to the one of the plurality of incident types. The method also includes determining, with the electronic processor, whether the image stream includes an object from the subset of objects of interest and generating, with the electronic processor, a notification associated with the object when the image stream includes the object. The notification is then transmitted, with a transmitter electrically coupled to the electronic processor, to a set of incident scene devices associated with the incident.

Another embodiment provides a computing device including a wireless transceiver and an electronic processor electrically coupled to the wireless transceiver. The electronic processor is configured to generate and store a list of objects of interest in a memory, where each object of interest in the list of objects of interest is mapped to at least one of a plurality of incident types. The electronic processor is also configured to receive an image stream of an incident and classify the image stream as one of the plurality of incident types. The electronic processor is further configured to select, from the memory, a subset of objects of interest from the list of objects of interest, the subset of objects of interest mapped to the one of the plurality of incident types. The electronic processor is also configured to determine whether the image stream includes an object from the subset of objects of interest and to generate a notification associated with the object when the image stream includes the object. The notification is transmitted with the transceiver to a set of incident scene devices associated with the incident.

FIG. 1 is a block diagram of an incident prediction system 100. In the example illustrated, the incident prediction system 100 includes a call controller 110. The call controller 110 may be, for example, a dispatch controller for a public safety organization. The call controller 110 communicates with a plurality of incident scene devices. The incident scene devices, for example, may be one or more host devices 120A through 120M via a communication network 140. On a singular basis, one of the host devices 120A through 120M may be referred to herein as a host device 120. The host devices 120A through 120M may be, for example, vehicle-mounted two-way radios, vehicle-mounted two-way radios with cameras (for example, dash-mounted cameras) or other sensing accessories or device or other similar communication and sensing devices.

The incident scene devices, for example, may further be one or more mobile communication devices 130A through 130N. On a singular basis, one of the mobile communication devices 130A through 130N may be referred to herein as a mobile communication device 130. The mobile communication devices 130A through 130N may be, for example, portable two-way radios, smart telephones, or other similar devices.

The communication network 140 may be a wired or a wireless communication network, such as a cellular network, a land mobile radio (LMR) network, or the like. Portions of the communication network 140 may be implemented using various wide area networks, for examples the Internet, and local area networks, for example, a Bluetooth™ network, a wireless local area network (for example, Wi-Fi), as well as a future developed networks, or a combinations or derivatives thereof.

FIG. 1 illustrates only one exemplary embodiment of an incident prediction system 100. In other embodiments, the incident prediction system 100 may include more or fewer components and may perform functions that are not explicitly described herein. In addition, although the call controller 110 is illustrated as communicating with the host devices 120A through 120M and mobile communication devices 130A through 130N via a single communication network 140, the call controller 110 may communicate with the host devices 120A through 120M and the mobile communication devices 130A through 130N via multiple communication networks (constructed in accordance with various network protocols) and connections (for example, wired or wireless connections). Further, although the incident prediction system 100 is shown as a centralized system, the incident prediction system 100 may also be implemented as a decentralized system in which the functionality of the call controller is accomplished within one or more of the incident scene devices.

Figure 2:
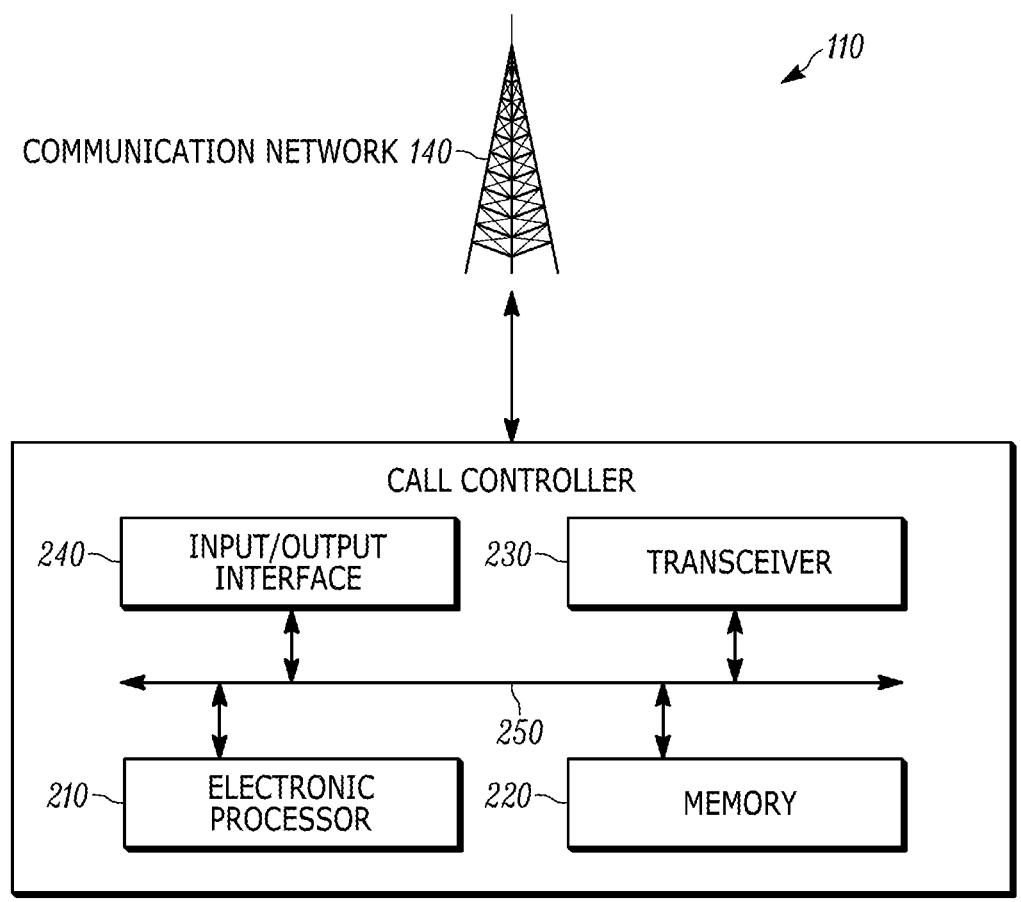
FIG. 2 is a block diagram of a call controller operating within a communication system in accordance with some embodiments.

FIG. 2 is a block diagram of one embodiment of the call controller 110. In the example illustrated, the call controller 110 includes an electronic processor 210, a memory 220, a transceiver 230, and an input/output interface 240. The electronic processor 210, the memory 220, the transceiver 230, and the input/output interface 240 communicate over one or more control and/or data buses (for example, a communication bus 250). FIG. 2 illustrates only one exemplary embodiment of a call controller 110. The call controller 110 may include more or fewer components and may perform functions other than those explicitly described herein.

In some embodiments, the electronic processor 210 is implemented as microprocessor with separate memory, such as the memory 220. In other embodiments, the electronic processor 210 may be implemented as a microcontroller (with memory 220 on the same chip). In other embodiments, the electronic processor 210 may be implemented using multiple processors. In addition, the electronic processor 210 may be implemented partially or entirely as, for example, a field-programmable gate array (FPGA), an application specific integrated circuit (ASIC), and the like and the memory 220 may not be needed or be modified accordingly. In the example illustrated, the memory 220 includes non-transitory, computer-readable memory that stores instructions that are received and executed by the electronic processor 210 to carry out functionality of the call controller 110 described herein. The memory 220 may include, for example, a program storage area and a data storage area. The program storage area and the data storage area may include combinations of different types of memory, such as a read-only memory and random-access memory.

The transceiver 230 enables wireless communication from the call controller 110 to, for example, the host devices 120A through 120M and the mobile communication devices 130A through 130N, via the communication network 140. In other embodiments, rather than the transceiver 230, the call controller 110 may include separate transmitting and receiving components, for example, a transmitter, and a receiver. In yet other embodiments, the call controller 110 may not include a transceiver 230 and may communicate with the host devices 120A through 120M and mobile communication devices 130A through 130N via a wired connection to the communication network 140.

As noted above, the call controller 110 may include the input/output interface 240. The input/output interface 240 may include one or more input mechanisms (for example, a touch screen, a keypad, a button, a knob, and the like), one or more output mechanisms (for example, a display, a printer, a speaker, and the like), or a combination thereof. The input/output interface 240 receives input from a user, provides output to a user, or a combination thereof. In some embodiments, as an alternative or in addition to managing inputs and outputs through the input/output interface 240, the call controller 110 may receive user input, provide user output, or both by communicating with an external device, such as a console computer, over a wired or wireless connection.

Figure 3:
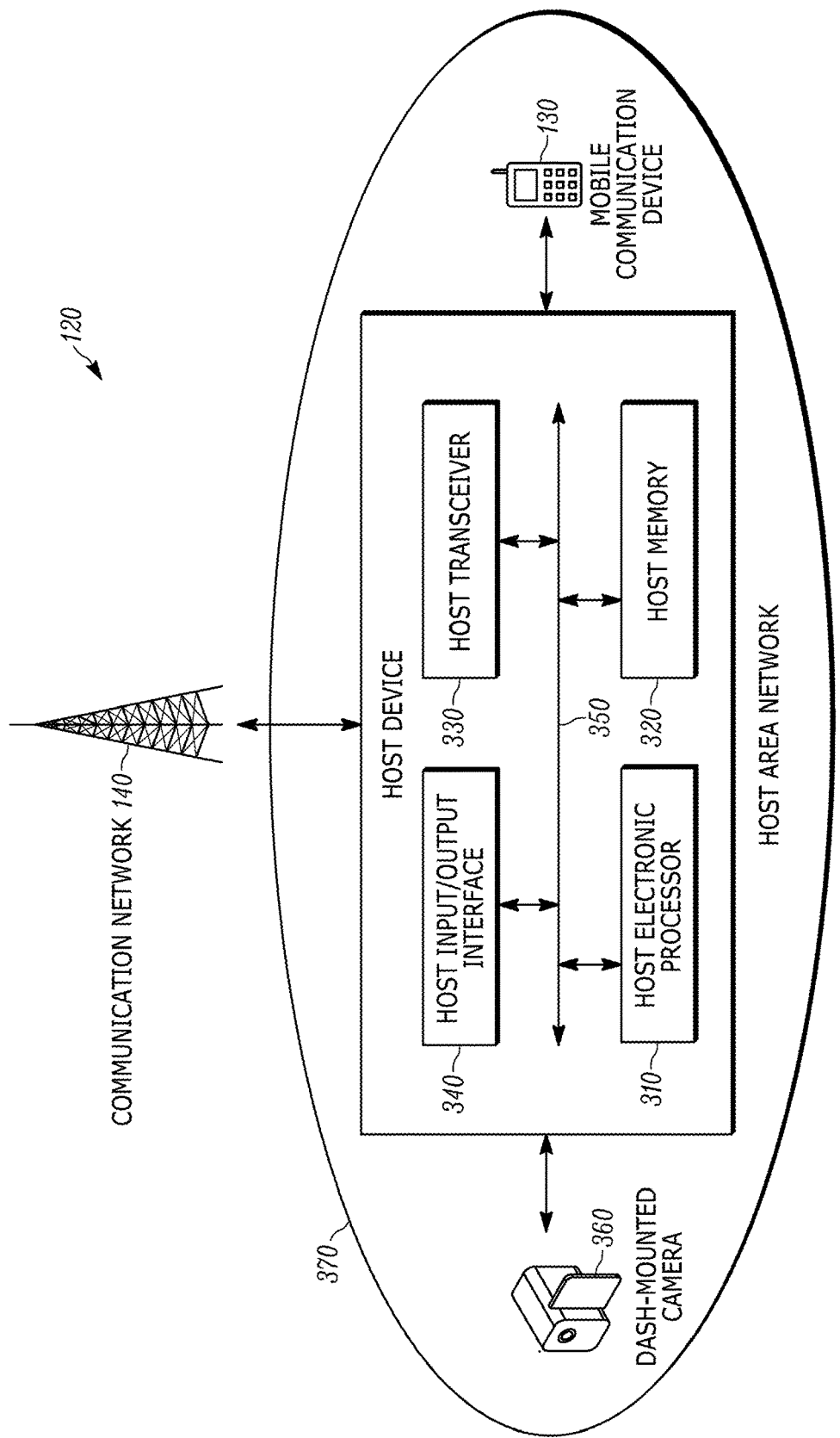
FIG. 3 is a block diagram of a host device operating within a communication system in accordance with some embodiments.

FIG. 3 is a block diagram of one embodiment of a host device 120. In the example illustrated, the host device 120 includes, among other things, a host electronic processor 310, a host memory 320, a host transceiver 330, and a host input/output interface 340. The host electronic processor 310, the host memory 320, the host transceiver 330, and the host input/output interface 340 communicate over one or more control and/or data buses (for example, a host communication bus 350). The host device 120 may include more or fewer components than illustrated and may perform additional functions other than those described herein.

The host electronic processor 310 may be implemented in various ways including ways that are similar to those described above with respect to the electronic processor 210. Likewise, the host memory 320 may be implemented in various ways including ways that are similar to those described with respect to the memory 220. The host memory 320 may store instructions that are received and executed by the host electronic processor 310 to carry out functionality described herein.

The host transceiver 330 enables wireless communication from the host device 120 to, for example, the call controller 110, mobile communication devices 130A through 130N, and/or host devices 120A through 120M, via the communication network 140. In other embodiments, rather than a host transceiver 330, the host device 120 may include separate transmitting and receiving components, for example, a transmitter, and a receiver.

The host input/output interface 340 may include one or more input mechanisms (for example, a touch screen, a keypad, a button, a knob, and the like), one or more output mechanisms (for example, a display, a speaker, and the like), or a combination thereof. In some embodiments, the host device 120 communicates with one or more external devices. The one or more external devices may include a dash-mounted camera 360, a mobile communication device 130, and the like. In one example implementation, the host device 120 is mounted in a vehicle (for example, a police vehicle), and communicates with a dash-mounted camera 360, a mobile communication device 130 of one or more individuals (for example, police officers) riding in the vehicle. The host device 120, the dash-mounted camera 360, and the mobile communication device 130 may form part of a host area network 370. The host area network 370 may be a communication network designed to work over a relatively short distance such as a Bluetooth® network or other near field communication protocol. In some embodiments, the dash-mounted camera 360 may communicate with the host device 120 over a wired connection. Even though it is possible for the communication network 140 and the host area network 370 to have similar capabilities, it is often the case that the communication network 140 has greater capabilities than the host area network 370 and that the communication network 140 may have higher bandwidth and range than the host area network 370.

The dash-mounted camera 360 may generate an image (for example, a still image) or image stream (for example, a video) of the environment around the dash-mounted camera 360. Instead of or in addition to the dash-mounted camera 360, other cameras or sensors may be communicate with the host device 120 including cameras and sensors embedded in mobile communication device 130 or worn in or on clothing.

Figure 4:
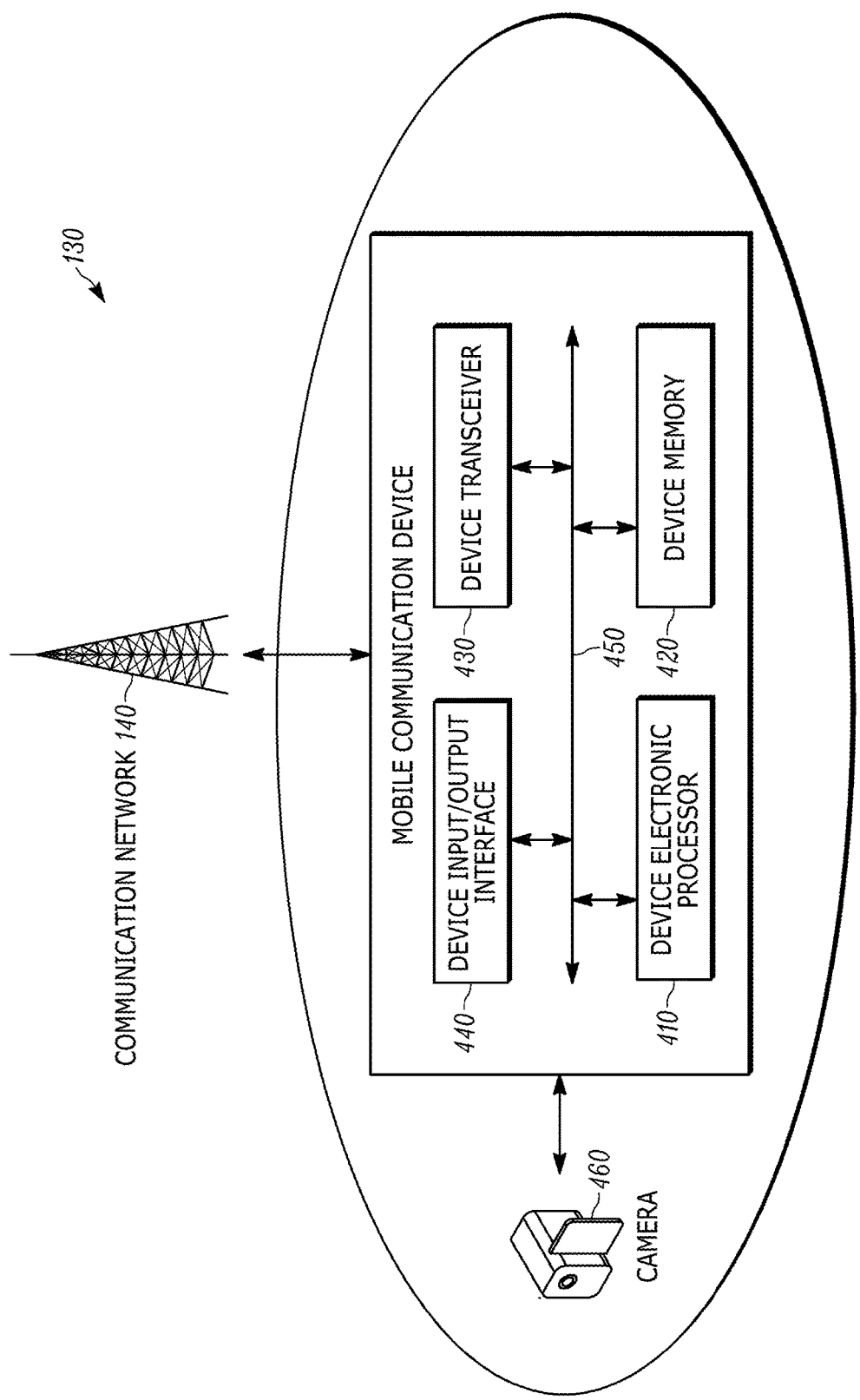
FIG. 4 is a block diagram of a mobile communication device operating within a communication system in accordance with some embodiments.

FIG. 4 is a block diagram of one embodiment of a mobile communication device 130. In the example illustrated, the mobile communication device 130 includes a device electronic processor 410, a device memory 420, a device transceiver 430, and a device input/output interface 440. The device electronic processor 410, the device memory 420, the device transceiver 430, and the device input/output interface 440 communicate over one or more control and/or data buses (for example, a device communication bus 450). As with other devices described herein, the mobile communication device 130 may include more or fewer components and may perform additional functions other than those described.

The device electronic processor 410 and the device memory 420 may be implemented in various ways including ways that are similar to those described above with respect to other processors and memory. Likewise, the device memory 420 may store instructions that are received and executed by the device electronic processor 410 to carry out functionality described herein.

The device transceiver 430 enables wireless communication from the mobile communication device 130 to, for example, the call controller 110, the host devices 120A through 120M, and/or other mobile communication devices 130A through 130N, via the communication network 140. In other embodiments, the mobile communication device 130 may include separate transmitting and receiving components, for example a transmitter, and a receiver.

The device input/output interface 440 may include components similar to those described with respect to the other input/output interfaces.

In the example illustrated, the mobile communication device 130 communicates with a camera 460 over a wired or wireless connection. In one example implementation, the mobile communication device 130 is a mobile two-way radio of a police officer, and it communicates with a body camera worn by the police officer. In some embodiments, the camera 460 may be included within the mobile communication device 130. Similar to the dash-mounted camera 360, the camera 460 may generate still images or an image stream of the environment around the camera 460.

Figure 5:
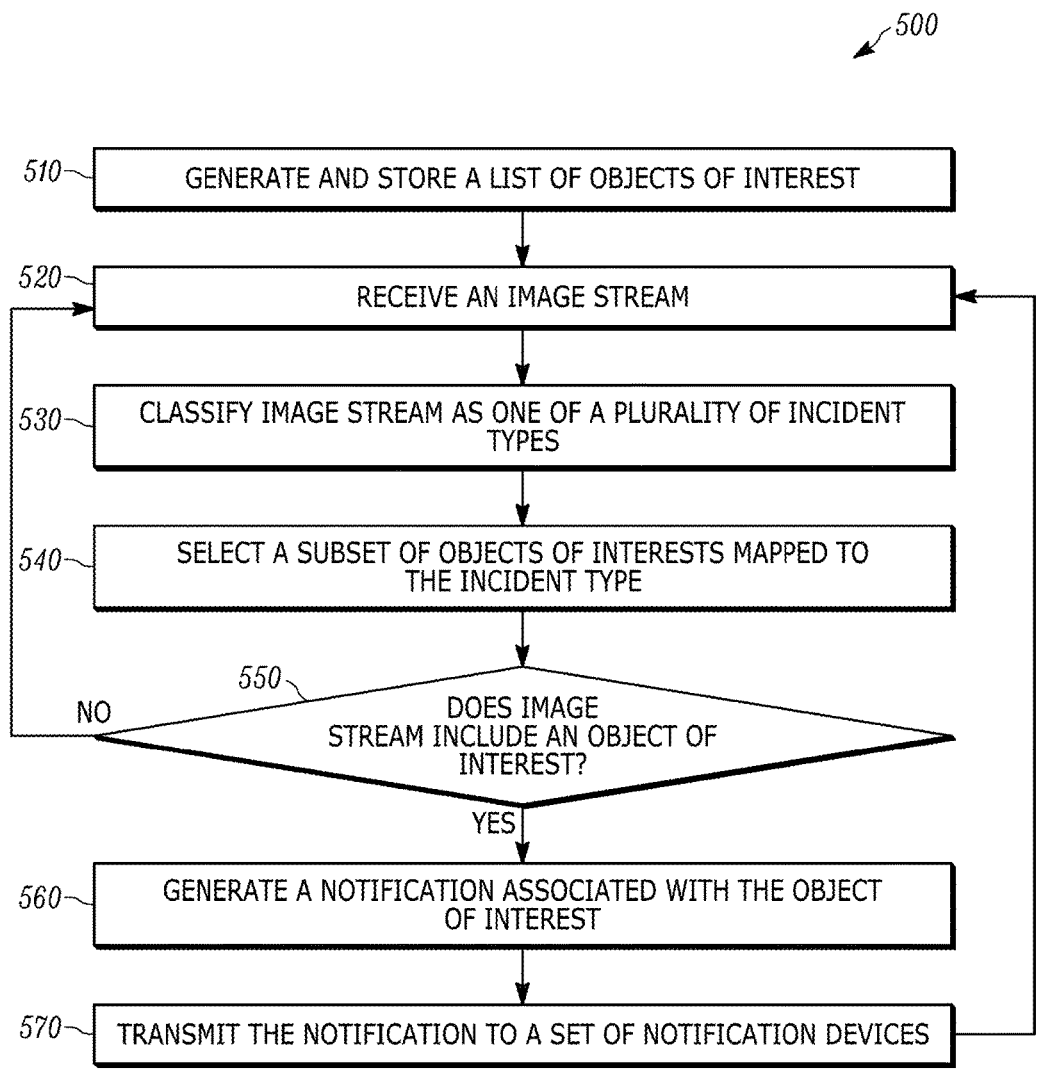
FIG. 5 is a flowchart of a method for incident situation prediction in accordance with some embodiments.

FIG. 5 is a flowchart illustrating one example method 500 of incident situation prediction. As illustrated in FIG. 5, the method 500 includes generating and storing a list of objects of interest (at block 510). For example, the call controller 110 may generate a list of objects of interest and store them in the memory 220 of the call controller 110. The objects of interest may be, for example, a fire extinguisher, a handgun, a chemical container, or other object that may be of interest to first responder, for example, because the object may be useful to a first responder task or pose a danger or hazard to a first responder.

In some embodiments, the list of objects of interest may be stored in the form of an incident table, where each object of interest is mapped to at least one of a plurality of incident types. Incident types may be, for example, a fire rescue, a mining operation, a search and rescue, and the like. Each incident type in the incident table is associated with a subset of the list of objects. The incident table may also include other information. For example, the incident table may include information mapping each object of interest to at least one of a plurality of notifications. In some embodiments, the incident table may include a notification mapped to detecting a plurality of objects of interest in succession. For example, the incident table may include information to generate a notification only when a second object of interest is detected after a first object of interest. The notification is, for example, a text message, an audio alert, a visual picture, flashing lights and the like. In another example, the incident table may include an image of the objects of interests. FIG. 6 illustrates an example of an incident table 600 that may be generated and stored in the memory 220 of the call controller 110. An incident table is only one exemplary technique of storing a list of objects of interest. Other techniques (for example, various database structures) may be used.

In some embodiments, the list of objects of interest is generated based on historical data available for an organization. For example, an object of interest may be added to the list of objects of interest upon determining that the object of interest is included in an image stream (for example, a second image stream) received for a previous incident of the organization. In some embodiments, an object of interest may only be included in the list of objects of interest when the object of interest created or had the potential to create a dangerous or helpful situation in a previous incident of the organization.

In some embodiments, a list of objects of interest may be specifically pre-loaded for an incident and used for the incident in place of a common list of objects of interest. For example, an organization may perform a planned operation and may generate a specific list of objects of interest for the planned operation. The specific list of objects of interest generated for the planned operation may include additional or fewer objects than a common list of objects of interest. In some embodiments, the call controller 110 may not have a common list of objects of interest. In these situations, a specific list of objects of interest may be generated and stored prior to and/or during every incident.

In some embodiments, the list of object of interest is transmitted to the host devices 120A through 120M and/or to the mobile communication devices 130A through 130N. In these situations, the call controller 110 may transmit the list of objects of interest to a host device 120 and/or a mobile communication device 130 when a user of the host device 120 and/or the mobile communication device 130 is participating in the incident. For example, in a fire rescue operation, a talkgroup may be formed with the participating host devices 120 and mobile communication devices 130 and the list of objects of interest may be transmitted to all or some of the devices included in the talkgroup. In some embodiments, the list of objects of interest may be generated on a host device 120 or a mobile communication device 130 and transmitted to the call controller 110 or other host devices 120 and mobile communication devices 130.

The method 500 also includes receiving an image stream (at block 520). The call controller 110 receives the image stream generated by, for example, the dash-mounted camera 360 or the camera 460 over the communication network 140. In some embodiments, the call controller 110 receives an image stream generated by some or all the dash-mounted cameras 360 and the cameras 460 that are present at an incident site or location. In some embodiments, the call controller 110 communicates directly with the dash-mounted camera 360 and/or the camera 460 over the communication network 140. In other embodiments, the host device 120 transmits the image stream generated by the dash-mounted camera 360 and the mobile communication device 130 transmits the image stream generated by the camera 460.

The method 500 includes classifying the image stream as one of a plurality of incident types (at block 530). For example, the call controller 110 may identify the incident type associated with the image stream. In some embodiments, the incident type associated with the image stream may be specified when the image stream is transmitted. For example, the incident type may be included in a header file sent with the image stream. In other embodiments, the incident type may be specified after the transmission of the image stream.

In some embodiments, the incident type may be received at the input/output interface 240 of the call controller 110 based on a selection made by a user. The input may be received after outputting the image stream and providing the list of incident types at the input/output interface 240. In other embodiments, the incident type may similarly be received at the host input/output interface 340 of the host device 120 or the device input/output interface 440 of the mobile communication device 130 and transmitted to the call controller 110 over the communication network 140 (for example, in a header file sent with the image stream).

Alternatively or in addition, the incident type may be automatically identified by the call controller 110, a host device 120, a mobile communication device 130, or another device communicating with the call controller 110. For example, the incident type may be automatically identified by analyzing the image stream using known recognition techniques and/or based on input from sensor devices communicating with the call controller 110.

Further, in some embodiments, the incident type may be identified based on the talkgroup and/or device that is transmitting the image stream. For example, the call controller 110 may identify the incident as a fire rescue when the image stream is received from a talkgroup formed for a fire rescue operation or the image stream is received from a mobile communication device 130 of a firefighter. In other embodiments, the incident type may be identified based on a location of a host device 120, the mobile communication device 130, the dash-mounted camera 360, or the camera 460.

After an incident type is identified, the method 500 includes selecting a subset of objects of interest mapped to the incident type (at block 540). As noted above, each object in the list of objects of interest is mapped to an incident type. The call controller 110 may select from the list of objects of interest (for example, the incident table shown in FIG. 6) all the objects of interest mapped to the incident type identified at block 530. In some embodiments, the call controller 110 may send the subset of objects of interest to the host device 120, and/or the mobile communication device 130.

After selecting a subset of objects of interest mapped to the incident type, the method 500 includes determining whether the image stream includes an object from the subset of objects of interest mapped to the incident type (at block 550). The image stream may be processed using known image analysis techniques for recognizing an object (or a portion thereof), such as by automatically identifying objects having a matching pattern, shape, size, color, or configuration as the object of interest in the list of objects of interest. In some embodiments, the call controller 110 may also store an image of the objects in the list of objects of interest. For example, the incident table may include an image of the objects as part of the incident table. The image analysis techniques may use the stored image to improve the speed and accuracy of recognition of the objects.

Devices or systems other than a call controller 110, a host device 120, or a mobile communication device 130 may identify an object of interest in an image stream. For example, in some embodiments, an image stream is transmitted (for example, over a wired or wireless connection) to an image processing device that processes the image stream to identify an object of interest in the image stream.

When the image stream includes an object from the subset of objects of interest mapped to the incident type, the method 500 generates a notification associated with the detected object of interest (at block 560). For example, the call controller 110 may transmit a notification associated with the object of interest detected in the image stream. The call controller 110 may determine the appropriate notification to be transmitted based on the list of object of interest stored in the memory 220 of the call controller 110.

In some embodiments, the list of objects of interest may include a notification that is mapped to a detected object only when the object is detected in a context. For example, the list of objects of interest may include a notification associated with a dangerous chemical only when the chemical is detected close to a fire. In these embodiments, the method 500 generates the notification only when the object of interest is detected in the listed context. The call controller 110 may detect a context in several ways, such as, based on the image stream, based on data received from a sensor, based on an electronic database store in a memory, and the like. For example, the call controller 110 may detect a chemical container in the image stream, detect a temperature of the incident from a temperature sensor, and determine that the chemical is flammable at a certain temperature from an electronic database (for example, a web page). The call controller 110 may then generate a notification when it detects that the sensed temperature is above the temperature at which the chemical is flammable.

In other embodiments, and as described above, the list of objects of interest includes a notification that is mapped to a detected object (for example, a second object) only when the object is detected after a first object is detected. In these embodiments, the method 500 generates a notification (for example, a second notification) only when the second object is detected after a first object is detected.

In some embodiments, each notification associated with an object in the list of objects of interest includes a plurality of severity levels. Further, each of the severity levels may raise a different alert on the host devices 120A through 120M and the mobile communication devices 130A through 130N. In some embodiments, the severity level of the notification may be associated with the location of the detected object with respect to the set of host devices 120A through 120M and the mobile communication devices 130A through 130N. For example, the detected object may be associated with a higher severity level notification when the object is within a predetermined distance from the set of mobile communication devices 130A through 130N and associated with a lower severity level notification when the object is outside the predetermined distance from the set of mobile communication devices 130A through 130N. In these embodiments, the call controller 110 may determine the location of objects with respect to the mobile communication devices 130A through 130N based on receiving location information from the mobile communication devices 130A through 130N and from the camera generating the image stream.

In other embodiments, the severity level of the notification is associated with the likelihood of the detected object causing injury. For example, a first object may have a higher likelihood of causing an injury than a second object. In these situations, the first object may include a notification of a higher severity level than the second object.

The method 500 then transmits the notification to the host devices 120A through 120M and the mobile communication devices 130A through 130N that are associated with the incident (at block 570). The call controller 110 may transmit a notification by transmitting an instruction to the host devices 120A through 120M and the mobile communication devices 130A through 130N over the communication network 140. The host devices 120A through 120M and the mobile communication devices 130A through 130N may generate an alert based on the instruction (that is, the notification) received from the call controller 110.

In some embodiments, a host device 120 or a mobile communication device 130 rather than the call controller 110 may generate the notification based on detecting an object of interest and transmit the notification to other host devices 120 and/or mobile communication devices 130.

In some embodiments, the notification may be transmitted only to a subset of the host devices 120A through 120M and a subset of the mobile communication devices 130A through 130N that are participating in the incident. The call controller 110 may determine which host device 120 and which mobile communication device 130 receives a notification. For example, the call controller 110 may transmit a notification only to the devices that are located near the object of interest detected in the image stream.

Returning to FIG. 5, the method 500 repeats (for example, continuously) to predict situations that may arise in the incident. The method 500 may be performed by the call controller 110, the host device 120, the mobile communication device 130, or a combination thereof.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM (Compact Disc Read Only Memory), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A method of incident situation prediction, the method comprising:
   generating and storing a list of objects of interest in a memory, where each object of interest in the list of objects of interest is mapped to at least one of a plurality of incident types;
   receiving, with a receiver, an image stream of an incident;
   classifying, with an electronic processor electrically coupled to the receiver, the image stream as one of the plurality of incident types;
   selecting, from the memory and with the electronic processor, a subset of objects of interest from the list of objects of interest, the subset of objects of interest mapped to the one of the plurality of incident types;
   determining, with the electronic processor, whether the image stream includes an object from the subset of objects of interest; and
   generating, with the electronic processor, a notification associated with the object when the image stream includes the object;
   transmitting, with a transmitter electrically coupled to the electronic processor, the notification to a set of incident scene devices associated with the incident.

2. The method of claim 1, further comprising:
   determining, with the electronic processor, whether the image stream includes a second object from the subset of objects of interest;
   generating, with the electronic processor, a second notification when the image stream includes both the object and the second object; and
   transmitting, with the transmitter, the second notification to the set of incident scene devices associated with the incident.

3. The method of claim 1, wherein generating and storing the list of objects of interest further comprises:
   determining that a second object is included in a second image stream received for a previous incident; and
   adding the second object to the list of objects of interest.

4. The method of claim 1, wherein the notification includes a plurality of severity levels.

5. The method of claim 4, wherein the severity level of the notification is based on a location of the object of interest with respect to the set of incident scene devices.

6. The method of claim 4, wherein the severity level of the notification is based on a likelihood of the object of interest causing injury.

7. The method of claim 1, wherein classifying the image stream as one of the plurality of incident types includes receiving the one of the plurality of incident types with the image stream.

8. The method of claim 1, wherein each object in the list of objects of interest is mapped to one of a plurality of notifications.

9. A communication device comprising:
   a wireless transceiver; and
   an electronic processor electrically coupled to the wireless transceiver and configured to:
   generate and store a list of objects of interest in a memory, where each object of interest in the list of objects of interest is mapped to at least one of a plurality of incident types;
   receive, with the wireless transceiver, an image stream of an incident;
   classify the image stream as one of the plurality of incident types;
   selecting, from the memory a subset of objects of interest from the list of objects of interest, the subset of objects of interest mapped to the one of the plurality of incident types;
   determine whether the image stream includes an object from the subset of objects of interest; and
   generate a notification associated with the object when the image stream includes the object;
   transmit, with the wireless transceiver, the notification to a set of incident scene devices associated with the incident.

10. The communication device of claim 9, wherein the electronic processor is further configured to:
    determine whether the image stream includes a second object from the subset of objects of interest;
    generate a second notification when the image stream includes both the object and the second object; and
    transmit, with the wireless transceiver, the second notification to the set of incident scene devices associated with the incident.

11. The communication device of claim 9, wherein the electronic processor configured to generate and store the list of objects of interest further includes:
    determining that a second object is included in a second image stream received for a previous incident; and
    adding the second object to the list of objects of interest.

12. The communication device of claim 9, wherein the notification includes a plurality of severity levels.

13. The communication device of claim 12, wherein the severity level of the notification is based on a location of the object of interest with respect to the set of incident scene devices.

14. The computing device of claim 12, wherein the severity level of the notification is based on a likelihood of the object of interest causing injury.

15. The computing device of claim 9, wherein classifying the image stream as one of the plurality of incident types includes receiving the one of the plurality of incident types with the image stream.

16. The computing device of claim 9, wherein each object in the list of objects of interest is mapped to one of a plurality of notifications.

* * * * *